US005624057A

United States Patent [19]

Lifshey

[11] Patent Number: 5,624,057
[45] Date of Patent: Apr. 29, 1997

[54] OPHTHALMIC PACKAGE AND DELIVERY DEVICE

[75] Inventor: Arthur L. Lifshey, East Brunswick, N.J.

[73] Assignee: Merck & Co., Inc., Rahway, N.J.

[21] Appl. No.: 432,500

[22] Filed: May 1, 1995

Related U.S. Application Data

[63] Continuation-in-part of Ser. No. 200,076, Dec. 22, 1993, abandoned.

[51] Int. Cl.$^6$ ...................................................... B65D 47/18
[52] U.S. Cl. ........................ 222/212; 222/420; 222/541.2; 604/216
[58] Field of Search ............................ 604/212, 216; 222/212, 83, 215, 541.2, 420

[56] References Cited

U.S. PATENT DOCUMENTS

| | | |
|---|---|---|
| 1,188,067 | 6/1916 | Greer . |
| 2,864,367 | 12/1958 | Mende . |
| 3,123,258 | 3/1964 | Schiltz . |
| 3,325,031 | 6/1967 | Singier . |
| 3,366,284 | 1/1968 | Marona et al. .......................... 222/211 |
| 4,168,032 | 9/1979 | Sneider . |
| 4,177,939 | 12/1979 | Thomas . |
| 4,787,536 | 11/1988 | Widerström ............................. 222/212 |
| 4,867,593 | 9/1989 | Kurokawa et al. . |
| 4,931,400 | 6/1990 | Jitsukawa . |
| 4,958,748 | 9/1990 | Otake . |
| 5,154,702 | 10/1992 | Foyil ...................................... 222/420 |
| 5,226,572 | 7/1993 | Gargione . |

Primary Examiner—Gregory L. Huson
Attorney, Agent, or Firm—Francis P. Bigley; Mark R. Daniel

[57] ABSTRACT

This invention consists of an ophthalmic storage and dispensing device formed by injection molding, consisting of a vial with thick rigid walls and a limited flexible area. The flexible area allows only a small displacement when squeezed providing a metered volume of dispensed liquid. It also has an integral molded dropper tip as well as an integral molded puncture membrane within the tip. A bottom plug, which serves as closure after filling, is sealed to the vial. The bottom plug is of varying size and shape so as to provide for varying internal liquid capacity in the same bottle. It can also have a separate cap which acts as both a seal break and reclosable mechanical liquid seal between usage periods. Both vial and cap offer a geometric shape which facilitates gripping and limits rolling.

5 Claims, 1 Drawing Sheet

5,624,057

OPHTHALMIC PACKAGE AND DELIVERY DEVICE

RELATED APPLICATION

The present patent application is a continuation-in-part application of application Ser. No. 08/200,076, filed Dec. 22, 1993 now abandoned.

TECHNICAL FIELD

This invention relates to a liquid dispensing device especially useful in the dispensing of ophthalmic drugs which typically need to be dispensed in droplet form.

BACKGROUND OF THE INVENTION

The present invention pertains to the an of liquid dispensers, and, more particularly, to a dispensing device for accurately dispensing small droplets of liquid. The invention is particularly applicable for use as an eyedropper and will be described with particular reference thereto although it will be appreciated that the invention has other and broader applications.

Medicament drop dispensers of the type to which the present invention pertains are available in various sizes and shapes for the numerous medicines and solutions which are available for the care and comfort of the human eye. Heretofore, such dispensers have basically comprised a relatively small compressible plastic container or vial provided with a dispensing nozzle and cap.

One problem associated with conventional eyedroppers is the difficulty in accurately controlling the amount of medicine dispensed, i.e., the number of drops dispensed. Most conventional eyedropper dispensers utilize one of two or a combination of these methods to achieve single drop control.

One method uses a highly compliant plastic bottle which the user squeezes to dispense a drop. The extensive deflection of the bottle creates a significant internal air pressure within the vial which expels the liquid through the tip or dispensing nozzle. In order to prevent a continuous stream of liquid medicament from being expelled, and to create single drops, these designs incorporate a flow restriction at the inlet of the tip or nozzle. Unfortunately, this flow restriction does not s limit the number of drops expelled during a single squeeze, but merely limits the liquid medicament flow rate flavoring the formation of individual drops releasing from the dropper tip rather than a continuous stream. It should be obvious that this flow restriction, if truly effective in preventing a stream of liquid, will also make the dispensing of drops more difficult, especially for older patients as well as those with physical disabilities. Also, the creation of a very small molded orifice, frequently as small as 0.005" (0.13 mm) in diameter creates manufacturing difficulties. In addition, the small orifice can be prone to clogging from particles of contamination sometimes drawn back into the bottle during usage or dried residue from the medicament formulation itself.

Another method often used is to manufacture a bottle with relatively rigid (relatively non-compliant) walls. With this configuration, the force to deflect or squeeze the bottle is relatively high compared to the compliant bottle of the previous paragraph. Because of this increased force necessary to deflect the plastic walls of the bottle, the user will tend to limit the squeezing action due to the difficulty encountered in the movement. However, increased force on the bottle will easily create a stream of liquid medicament to be expelled rather than a drop. Another disadvantage of this design is that it is frequently difficult to dispense even a single drop, especially for older patients as well as those with physical disabilities.

SUMMARY OF THE INVENTION

A package for storage and dispensing a liquid in droplet form is disclosed which comprises a vial, a cap member having an internal screw thread and a bottom plug, the vial being injection molded plastic and having a wall which forms a ovoid midsection, the ovoid midsection having a top and bottom, the top being formed to provide an integral reduced diameter neck portion, the bottom being open and circular and able to receive the bottom plug, the bottom plug being of different sizes and shapes to allow for variable liquid volume capacity while keeping the outside dimensions of the vial constant, the bottom plug being sealed to the vial; the ovoid midsection being further defined by two smaller radiused opposing segments and two larger radiused opposing segments, the smaller radiused opposing segments having a radius and axis corresponding to that of the circular bottom of the ovoid midsection, the larger radiused opposing segments having a significant radius So as to form an ovoid cross section, the axis of the larger radius opposing segments being parallel to the longitudinal axis of the vial, but offset in order to create an intersection defining the ovoid shape; the wall of the ovoid midsection being of a rigid plastic suitable for injection molding, a target area being confined to one of the larger radiused segments of the oval shaped cross section, the wall in the target area being thinner than the remainder of the vial wall, the central longitudinal portion of the target area being bounded on either side by longitudinal pleats which make the target area compliant and easy to push for small displacements, the longitudinal pleats terminating at the top and bottom of the ovoid midsection and terminating to the left and right where they are affixedly attached to the rigid thicker wall section, the transition to the left and right occurring at the intersection between the larger and the smaller radius of the ovoid midsection, the longitudinal pleats creating a spring action due to distortion of their original pleated shape during displacement; the neck portion having external helical screw threads mateingly adapted to engage the cap internal threads, the neck portion having at its further most end a nozzle having a barrier membrane across the opening; the cap member having an internal piercing point which may serve to open the barrier membrane of the nozzle.

The shape of the vial may vary but is generally ovoid or tubular. The walls of the package vary in thickness depending upon where on the vial they are measured. In general, the rigid walls range in thickness from about 1.0 mm to about 2.5 mm. However, in the target area, including the central longitudinal portion and the pleats, the thickness ranges from about 0.4 mm to about 0.8 mm. Any appropriate plastic material may be used to injection mold the vial. In particular, polyethylene or polypropylene perform well.

BRIEF DESCRIPTION OF THE DRAWINGS

The invention may take physical form in certain parts and arrangement of parts, a preferred embodiment of which will be described in detail in this specification and illustrated in the accompanying drawings wherein.

DETAILED DESCRIPTION OF THE INVENTION

Figure 2:
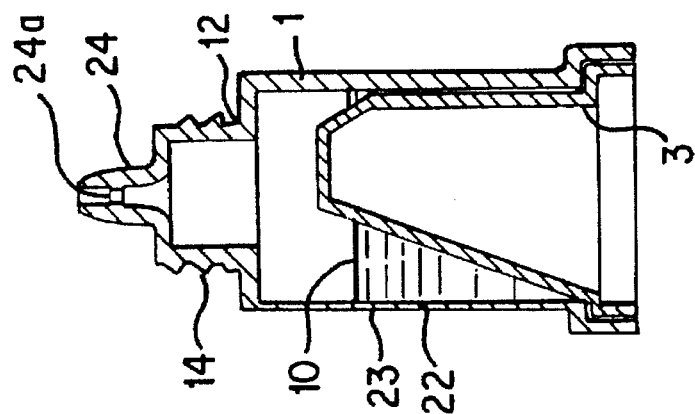
FIG. 2 is a side sectional view of a similar ophthalmic container, but illustrating a variant bottom plug, wherein the plug is produced with a longer protrusion into the bottle so that the internal volume of the package is reduced. One face of the plug may be angled to provide clearance for movement of the target area and for proper visual level indication through the thinner target area.
Figure 1:
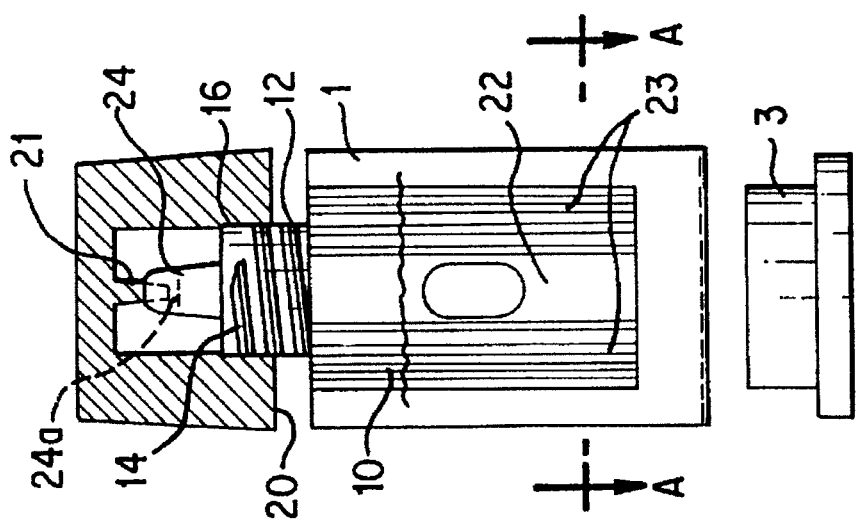
FIG. 1 is a diagrammatic view of the ophthalmic container including bottom plug and cap.

A package for storage and dispensing a liquid in droplet form is disclosed which comprises a vial (1), a cap member (20) having an internal screw thread (16) and a bottom plug (3), the vial (1) being injection molded and having a wall which forms an ovoid midsection, the ovoid midsection having a top and bottom, the top being formed to provide an integral reduced diameter neck portion (12), the bottom being open and circular and able to receive the bottom plug (3), the bottom plug (3) being of different sizes and shapes to allow for variable liquid volume capacity while keeping the outside dimensions of the vial (1) constant, the bottom plug (3) being sealed to the vial (1); the ovoid midsection being further defined by two smaller radiused opposing segments (1a) and two larger radiused opposing segments, (1b, 1c) the smaller radiused opposing segments (1a) having a radius and axis corresponding to that of the circular bottom of the ovoid midsection, the larger radiused opposing segments (1b, 1c) having a significant radius so as to form an ovoid cross section, the axis of the larger radius opposing segments being parallel to the longitudinal axis of the vial, but offset in order to create an intersection defining the ovoid shape; the wall of the ovoid midsection being of a rigid plastic suitable for injection molding, the target area (22) being confined to a larger radiused section (1c) of the oval shaped cross section, the wall in the target area (22) being thinner than the remainder of the vial wall, the central longitudinal portion of the target area (22) being bounded on either side by longitudinal pleats (23) which make the target area (22) compliant and easy to push for small displacement, the longitudinal pleats (23) terminating at the top and bottom of the ovoid midsection and terminating to the left and right where they are affixedly attached to the rigid thicker wall section, the transition to the left and right occurring at the intersection between the larger and the smaller radius of the ovoid midsection, the longitudinal pleats creating a spring action due to distortion of their original pleated shape during displacement; the neck portion (12) having external helical screw threads (14) mateingly adapted to engage the cap internal threads (16), the neck portion (12) having at its further most end a nozzle (24) having a barrier membrane (24a) across the opening; the cap member (20) having an internal piercing point (21 ) which may serve to open the barrier membrane of the nozzle.

The shape of the vial may vary but is generally ovoid or tubular. The walls of the package vary in thickness depending upon where on the vial they are measured. In general, the rigid walls range in thickness from about 1.0 mm to about 2.5 mm. However, in the target area, including the central longitudinal portion and the pleats, the thickness ranges from about 0.4 mm to about 0.8 mm. Any appropriate material may be used to injection mold the vial. In particular, polyethylene or polypropylene perform well.

The present invention contemplates a new and improved dispenser device for dispensing droplets of liquid which overcomes the above-referenced difficulties and provides a liquid medicament dispenser which accurately dispenses droplets of liquid medicament at desired locations without waste.

In accordance with the present invention, there is provided an improved drop dispenser for use with a closed compressible container, which dispenser is comprised of a tubular or ovoid dispenser member having walls formed by relatively rigid and thick plastic. There is, however, incorporated into this bottle, a relatively small target area which is much more compliant than the remainder of the bottle. In the preferred embodiment of this invention, this target area consists of a combination of longitudinal pleats and thinner wall sections which make the target area compliant and easy to push, but only for small displacements. After the small displacement, the squeezing force becomes very high and difficult to overcome manually. This limited displacement of the target area is just sufficient to easily dispense a single drop. The user must release pressure on the bottle, allowing the plastic in the target area to return to its non-displaced position before again pushing to dispense the next single drop.

Although the preferred embodiment uses longitudinal pleats, other geometric variations to achieve the same means are also part of this invention. Other methods for creating the target area are: thinner walls alone, pleats alone, insertion of a lower flexural modulus or more compliant material by molding or welding in place.

Another advantage of this invention is that the relatively thick walls existing everywhere except in the small target area make this bottle much more resistant to water vapor or oxygen permeation, which provides longer shelf life for the liquid medicament. Another advantage is that this lower permeation allows the usage of a larger size, easy-to-handle bottle even for low fill volumes of liquid medicament.

Another feature of this invention is that the target area provides a convenient visible liquid level indicator for the patient.

Another feature of this invention utilizes bottom plug of different lengths and shapes to allow various fill levels (10) in the same bottle without creating excessive empty (air) space in the vial. This is important with certain sensitive formulations. This feature is accomplished by varying the height and shape of the plug. For example, the plug may be conical, cut on an angle or cylindrical. When cut on an angle, the angled surface may range from zero degrees to just less than 90 degrees from the horizontal.

Another feature of this invention is that the patient can use the bottom plug as an alterative (to the target area) dispensing button, with the same single-drop dispensing advantages.

It will also be appreciated that both the bottom plug and the nozzle can be hermetically sealed further insuring the stability and integrity of the contents.

The cap can also serve as a "seal-break cap." The nozzle can be formed with a barrier membrane across the opening. The inside of the cap fitting over this nozzle can be fitted with a suitably sized and shaped piercing point. The cap can be designed so that an initial half-turn of the cap punctures the nozzle barrier. Attentively, the cap and bottle may be so designed so that the cap is pushed to break the seal. The barrier membrane may also be external to, but molded integrally with the nozzle. Upon initially unscrewing the cap in the normal (counter-clockwise) manner, the cap first severs the seal, allowing drops to be later dispensed after full removal of the cap.

The cap or bottle can also be fitted with external tabs, wings, flanges, or other molded features which serve as a tamper-evidence device.

Preferably, the thinner target area is formed simultaneously when the dispenser is molded, using suitable injection molding techniques.

Current ophthalmic packages utilize either injection blow molding, extrusion blow molding, or extrusion blow molding with in-place filling, often called blow-fill-seal. With all of these blow molding processes, there is only limited control over the final molded geometry and wall thickness of the part. The disadvantages lie in the fact that it is difficult to mix different geometrics and wall sections in the same part to custom design for desired performance and dispensing characteristics. However, with injection molding it is possible and should be part of the invention.

With injection molding, there is complete control over geometry and wall thickness. This subject invention is able to combine thick-walls for very low overall water vapor transmission, selective flexibility for easy dispensing, side or bottom dispensing, limited displacement for single drop control, single outside image for all fill volumes, and desirable hermetic seals, easy patient opening, and integral tamper evidence.

As a result of the above described design, this package provides: (1) low-cost high-speed production; (2) one size outer image for all liquid fill levels; (3) low permeation weight loss which is related to longer shelf life; (4) easy one-drop dispensing; (5) easy grip roll resistant bottle; (6) easy open tamper evident vial; (7) hermetically sealed, volume adjustable plug; (8) side or bottom dispensing; (9) single drop dispensing; and (10) suitability for in-line molding/sterilization/ filling/sealing/labeling.

Injection molding is utilized in the production of this device. Injection molding permits the formation of a separate thin-walled target area having greater flexibility than the surrounding relatively rigid and thick wall of the container.

Figure 3:
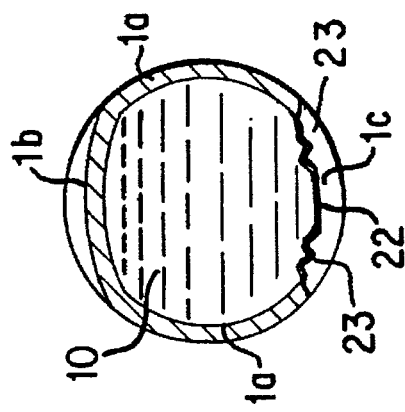
FIG. 3 is a cross-section of either container of FIGS. 1 or 2, taken along line A—A of FIG. 1.

The vial (1) is generally formed of a rigid, relatively thick walled plastic suitable for injection molding such a polyethylene, polypropylene, or the like. According to the preferred embodiment shown cross-section in FIG. 3, there is a target area (22) located in the convex side wall of the container. This target area is positioned in a larger radiused section of the oval-shaped cross-section (1c). This target area could also be located in any flat, concave or other area of the container.

Through the use of any combination of geometric variations in the wall section, a small area of increased flexibility is created in the otherwise rigid container. In the preferred embodiment illustrated in FIG. 3, the target area is created through combination of thinner wall sections and straight pleats which are easily injection molded.

By whatever geometric means created, this more flexible target area allows the user to easily depress the container, but only through a very limited displacement. After this limited displacement, sufficient to expel a single drop, the force to create further displacement increases rapidly, making the expulsion of a second drop difficult without full release and reapplication of the squeezing pressure.

Although this preferred embodiment provides for the dispensing of a single eye drop, this just described mechanical action can be adjusted to allow for the dispensing of any desired dosage from a single drop (approximately 30 to 50 microliters), the multiple drops, or even larger non-droplet dosages as high as 25 milliliters (cc.) by adjusting the container size and geometry and wall thickness.

What is claimed is:

1. A package for a storage and dispensing of a liquid in droplet form comprising a vial, a cap member having an internal screw thread and a bottom plug, the vial being injection molded and having a wall which forms an ovoid midsection, the ovoid midsection having a top and bottom, the top being formed to provide an integral reduced diameter neck portion, the bottom being open and circular and able to receive the bottom plug, the bottom plug being of different sizes and shapes to allow for various fill levels while keeping the outside dimension of the vial constant, the bottom plug being sealed to the vial; the ovoid midsection being further defined by two smaller radiused opposing segments and two larger radiused opposing segments, the smaller radiused opposing segments having a radius and axis corresponding to that of the circular bottom of the ovoid midsection, the larger radiused opposing segments having a significant radius so as to form an ovoid cross section, the axis of the larger radiused opposing segments being parallel to the longitudinal axis of the vial, but offset in order to create an intersection defining to ovoid shape; the wall of the ovoid midsection being of a rigid plastic suitable for injection molding, a target area being confined to one of the larger radiused segments of the oval shaped cross section, the wall in the target area being thinner than the remainder of the vial wall, the central longitudinal portion of the target area being bounded on either side by longitudinal pleats which make the target area compliant and easy to push for small displacements, the longitudinal pleats terminating at the top and bottom of the ovoid midsection and terminating to the left and right where they are affixedly attached to the rigid thicker wall section, the transition to the left and right occurring at the intersection between the larger and the smaller radius of the ovoid midsection, the longitudinal pleats creating a spring action due to distortion of their original pleated shape during displacement; the neck portion having external helical screw threads mateingly adapted to engage the cap internal threads, the neck portion having at its further most end a nozzle having a barrier membrane across the opening; the cap member having an internal piercing point which may serve to open the barrier membrane of the nozzle.

2. The package of claim 1 wherein, the shape of the vial is ovoid or tubular.

3. The package of claim 1 wherein the rigid walls range in thickness from about 1.0 mm to about 2.5 mm.

4. The package of claim 1 wherein the target area and pleats range in thickness from about 0.4 mm to about 0.8 mm.

5. The package of claim 1 wherein the injection molded material is polyethylene or polypropylene.

* * * * *